United States Patent [19]

Homan et al.

[11] 4,269,991
[45] May 26, 1981

[54] NOVEL MERCAPTOORGANOSILOXANES

[75] Inventors: Gary R. Homan, Midland, Mich.; Louis H. Toporcer, Twinsburg, Ohio

[73] Assignee: Dow Corning Corporation, Midland, Mich.

[21] Appl. No.: 99,251

[22] Filed: Dec. 3, 1979

[51] Int. Cl.³ .............................. C07F 7/08; C07F 7/18
[52] U.S. Cl. ..................................................... 556/427
[58] Field of Search ........................................... 556/427

[56] References Cited

U.S. PATENT DOCUMENTS

| | | | |
|---|---|---|---|
| 2,865,884 | 12/1958 | DeBenneville et al. | 556/427 X |
| 3,532,729 | 10/1970 | Cekada et al. | 556/427 |
| 4,033,934 | 7/1977 | Berger | 556/427 X |

FOREIGN PATENT DOCUMENTS 2406399  9/1974  Fed. Rep. of Germany ........... 556/427

Primary Examiner—Paul F. Shaver
Attorney, Agent, or Firm—Roger H. Borrousch

[57]    ABSTRACT

Novel mercaptoorganosiloxane compounds of the formula

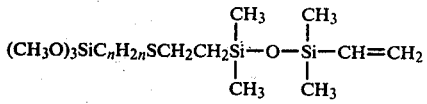

wherein n has a value of from 1 to 3 inclusive, are useful as components of primer compositions for enchancing the adhesion of silicone elastomers to substrates.

4 Claims, No Drawings

NOVEL MERCAPTOORGANOSILOXANES

BACKGROUND OF THE INVENTION

1. Field of the Invention

The present invention relates to novel sulfur-containing siloxane compounds and to compositions including the compounds which are useful as primers for promoting adhesion of silicone elastomers to substrates.

2. Description of the Prior Art

Adhesion of silicone elastomers, e.g. sealant compositions, to substrate surfaces has been the subject of substantial research and developmental work in the past. Of particular concern has been the enhancement of adhesion characteristics for elastomers formed by the platinum catalyzed reaction of vinyl endblocked siloxane polymers and ≡SiH-group-containing materials which proceeds according to the generalized reaction:

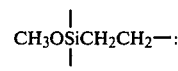

SUMMARY OF THE INVENTION

The present invention provides compounds of the formula

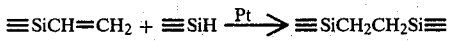

wherein n has a value of from 1 to 3 inclusive, which compounds are formed by the reaction of 1,1,3,3-tetramethyl-1,3-divinyldisiloxane and a selected mercaptoalkyltrimethoxysilane. A preferred compound, 1-(7,7,-dimethoxy-8-oxa-3-thia-7-silanonyl)-1,1,3,3-tetramethyl-3-vinyldisiloxane is formed by the reaction of 1,1,3,3-tetramethyl-1,3-divinyldisiloxane and gamma mercaptopropyltrimethoxy silane. The compounds are employed in the development of primer formulations to enhance adhesion characteristics of silicone elastomer sealant compositions to surfaces of substrates, especially.

Incorporated by reference herein is U.S. Patent application Ser. No. 99,300, by Gary R. Homan and Chi-Long Lee, filed concurrently herewith and entitled "Mercaptoorganopolysiloxane and Curable Compositions Including Same", and U.S. Patent application Ser. No. 99,303, by Gary R. Homan and Jan M. Blevins, filed concurrently herewith and entitled "Novel Mercaptoorganopolysiloxanes".

DESCRIPTION OF THE INVENTION

EXAMPLE 1

1-(7,7-dimethoxy-8-oxa-3-thia-7-silanonyl)-1,1,3,3-tetramethyl-3-vinyldisiloxane was prepared according to the following process. Two and one-half moles (490 grams) of gamma mercaptopropyltrimethoxy silane was added to a 1-liter flask. A portion of a total quantity of one mole (186 grams) of 1,1,3,3-tetramethyl-1,3-divinyldisiloxane was added to the flask, resulting in the immediate formation of a bluegreen color and generation of heat. The flask was placed in a hood and stirred. The exotherm was measured at 75° C, subsided to about 55° C. and remained there for 10 minutes. The remaining 1,1,3,3-tetramethyl-1,3-divinyldisiloxane was added with no further exotherm. Gas/liquid chromotography revealed consumption of substantially all of the 1,1,3,3-tetramethyl-1,3-divinyldisiloxane reagent and the presence of mono- and diadduct products. The reaction product was distilled through a Vigreaux column to yield 60 g of approximately 95% pure product having a boiling point of 157° C. at 3.0 mm Hg.

Infrared analysis of the product confirmed the structure, i.e.,

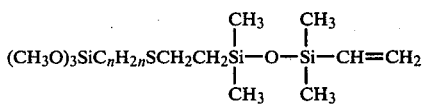

—Si(CH$_3$)$_2$OSi(CH$_3$)$_2$CH=CH$_2$: 1595, 1405, 1250, 1050, 1005, 955, 840, 785 and 520 cm$^{-1}$ A sample of the product was introduced directly into a mass spectrometer and heated to 200° C. at 10$^{-6}$ torr and the analysis was also in agreement with the structure, i.e., M$^+$ at m/e 382, m$^+$—CH$_3$ at m/e 367, m$^+$—CH=CH$_2$ at m/e 355, CH$_2$=CHSi(CH$_3$)$_2$OSi(CH$_3$)$_2$— at m/e 159 and (CH$_3$O)$_3$Si— at m/e 121.

The H$^+$ nmr spectrum also agrees with the structure. The proton ratio indicated that some disulfide product had been formed.

| | Proton Ratio | δValues |
|---|---|---|
| —CH=CH$_2$ | 2.9 | 5.6-6.2 |
| CH$_3$O— | 9.2 | 3.5 |
| —SCH$_2$— | 3.8 | ~2.5 |
| | 2.5 | ~1.6 |
| —SiCH$_2$CH$_2$—* | | |
| —SiCH$_2$— | 4.2 | — |
| —SiCH$_3$ | 11.4 | 1.3, 0.09 |

The foregoing reaction process may suitably be carried out in the presence of ferric 2-ethylhexanoate (octoate) or suitable free radical generating catalysts, as well as with use of radiant energy (e.g., ultraviolet).

In a like manner, the foregoing general process may be employed to prepare the corresponding 1-(6,6-dimethoxy-7-oxa-3-thia-6-silaoctyl)-1,1,3,3-tetramethyl-3-vinyldisiloxane and 1-(5,5-dimethoxy-6-oxa-3-thia-5-silaheptyl)-1,1,3,3-tetramethyl-3-vinyldisiloxane compounds through substitution of the appropriate mercaptoethyl and mercaptomethyl substituted silanes as reactants.

EXAMPLE 2

Two primer formulations were prepared by using the compound of Example 1. The constituents of the formulations in parts by weight were as follows:

| Component | No. 1 | No. 2 |
|---|---|---|
| Toluene | 57 parts | 57 parts |
| Example 1 compound | 1 part | 1 part |
| Ethylpolysilicate | 1 part | 1 part |

-continued

| Component | No. 1 | No. 2 |
|---|---|---|
| Bis (acetylacetonyl) diisopropyltitanate | 1 part | 1 part |
| Platinum Complex[1] | — | 0.3 parts |

The two formulations were applied to various substrates and qualitatively graded in terms of capacity to enhance the adhesion of Silastic ® E silicone rubber, room temperature vulcanizing sealant. The results of the qualitative grading, represented in terms of percent cohesive failure, are set out in Table 1.

TABLE 1

| Substrate | Percent Cohesive Failure | |
|---|---|---|
|  | Formulation No. 1 | Formulation No. 2 |
| Aluminum | 100 | 50 |
| Anodized Aluminum | 100 | 100 |
| Stainless Steel | 100 | 100 |
| Polycarbonate | 0 | 0 |

EXAMPLE 3

A lap shear was performed according to ASTM C 273-61. The primer composition prepared according to Formulation No. 1 of Example 2 was wiped onto precleaned aluminum panels and allowed to set for one hour. A Silastic ® E silicone rubber sealant was prepared and applied to the primed and unprimed (control) panels. The rubber was cured at 150° C. for one-half hour. Adhesive strengths for five primed and unprimed samples were determined on an Instron tester. The average adhesive strength of the unprimed samples was 172 kilopascals while the average adhesive strength of the primed samples was 1400 kilopascals.

Numerous modifications and variations in the foregoing preparative process as well as the foregoing formulation of primer compositions are expected to occur to those of ordinary skill in the art. Consequently only such limitations as appear in the appended claims should be placed on the invention.

What is claimed is:

1. A compound of the formula,

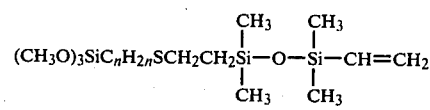

wherein n has a value of from 1 to 3 inclusive.

2. A compound according to claim 1, 1-(7,7-dimethoxy-8-oxa-3-thia-7-silanonyl)-1,1,3,3-tetramethyl-3-vinyldisiloxane.

3. A compound according to claim 1, 1-(6,6-dimethoxy-7-oxa-3-thia-6-silaoctyl)-1,1,3,3-tetramethyl-3-vinyldisiloxane.

4. A compound according to claim 1, 1-(5,5-dimethoxy-6-oxa-3-thia-5-silaheptyl)-1,1,3,3-tetramethyl-3-vinyldisiloxane.

* * * * *

UNITED STATES PATENT AND TRADEMARK OFFICE
CERTIFICATE OF CORRECTION

PATENT NO. : 4,269,991
DATED : May 26, 1981
INVENTOR(S) : G. R. Homan et al.

It is certified that error appears in the above-identified patent and that said Letters Patent is hereby corrected as shown below:

Column 2, after the formula

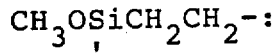

insert "2840, 1455, 1340, 1190, 1090, 805 and 460 $cm^{-1}$"

Column 3, Table Under Example 2 - add the following footnote:
"(1) A divinyltetramethylsiloxane complex of chloroplatinic acid as set out in U.S. Patent No. 3,419,573."

Abstract - the word "enchancing" should read "enhancing"

Signed and Sealed this

Fourteenth Day of June 1983

[SEAL]

Attest:

DONALD J. QUIGG

Attesting Officer    Acting Commissioner of Patents and Trademarks